(12) United States Patent
Ni et al.

(10) Patent No.: US 6,514,251 B1
(45) Date of Patent: Feb. 4, 2003

(54) COOLED-WET ELECTRODE

(75) Inventors: Yicheng Ni, Herent (BE); Yi Miao, Nanjing (CN); Guy Marchal, Oud-Heverlee (BE)

(73) Assignee: K.U. Leuven Research & Development, Leuven (BE)

( * ) Notice: Subject to any disclaimer, the term of this patent is extended or adjusted under 35 U.S.C. 154(b) by 0 days.

(21) Appl. No.: 09/762,728

(22) PCT Filed: Aug. 13, 1999

(86) PCT No.: PCT/BE99/00106

§ 371 (c)(1),
(2), (4) Date: May 1, 2001

(87) PCT Pub. No.: WO00/09208

PCT Pub. Date: Feb. 24, 2000

(30) Foreign Application Priority Data

Aug. 14, 1998 (NL) .............................................. 1009868

(51) Int. Cl.[7] .............................................. A61B 18/18

(52) U.S. Cl. .............................. 606/41; 606/45; 606/48

(58) Field of Search .............................. 606/41, 45, 46, 606/47, 48, 49, 50

(56) References Cited

U.S. PATENT DOCUMENTS

| 5,472,441 A | 12/1995 | Edwards et al. ............... 606/41 |
| 5,688,267 A | * 11/1997 | Panescu et al. ................ 606/31 |
| 6,106,524 A | * 8/2000 | Eggers et al. .................. 606/41 |

FOREIGN PATENT DOCUMENTS

| EP | 0115420 | 8/1984 |
| WO | 9632051 | 10/1996 |
| WO | 9803220 | 1/1998 |

OTHER PUBLICATIONS

Lorentzen, T. "A Cooled Needle Electrode for Radiofrequency Tissue Ablation: Thermodynamics Aspects of Improved Performance Compared with Conventional Needle Design," *Academic Radiology* 3(7): 556–563 (1996).

Rossi, S. et al. "Percutaneous Treatment of Small Hepatic Tumors by an Expandable RF Needle Electrode," *American Journal of Roentgenology* 170(4): 1015–1022 (1998).

Patterson, E. et al. "Radiofrequency Ablation of Porcine Liver In Vivo: Effects of Blood Flow and Treatment Time on Lesion Size," *Annals of Surgery* 227(4): 559–565 (1998).

Miao, Y. et al. "Ex Vivo Experiment on Radiofrequency Liver Ablation with Saline Infusion through a Screw–Tip Cannulated Electrode," *Journal of Surgical Research* 71: 19–24 (1997).

Goldberg, S.N. et al. "Large–Volume Tissue Ablation with Radio Frequency by Using a Clustered, Internally Cooled Electrode Technique: Laboratory and Clinical Experience in Liver Metastases," *Radiology* 209: 371–379 (1998).

Goldberg, S.N. et al. "Tissue Ablation with Radiofrequency: Effect of Probe Size, Gauge, Duration, and Temperature on Lesion Volume," *Academic Radiology* 2(5): 399–404 (1995).

Goldberg, S.N. et al. "Radio–Frequency Tissue Ablation of VX2 Tumor Nodules in the Rabbit Lung," *Academic Radiology* 3(11): 929–935 (1996).

* cited by examiner

*Primary Examiner*—Rosiland S. Kearney
(74) *Attorney, Agent, or Firm*—Webb Ziesenheim Logsdon Orkin & Hanson, P.C.

(57) ABSTRACT

Device for delivering radio frequency (RF) energy, for example during tissue ablation procedures, comprising an electrode having a distal end associated with tissue puncturing means and a proximal end connectable to a radio frequency energy source, wetting means for wetting the proximity of the distal end of the electrode with a non-toxic (RF) conductive solution and cooling means for cooling at least the distal end of the electrode. The invention further relates to a process for cooling and wetting a radio frequency energy delivering device and to a guidance element therefor.

10 Claims, 5 Drawing Sheets

COOLED-WET ELECTRODE

BACKGROUND OF THE INVENTION

1. Field of the Invention

The invention relates to novel devices for delivering radio frequency energy (RF), for example during tissue ablation procedures.

The invention relates in particular to a novel concept of an electrode for the optimization of radio frequency ablation. This concept will hereunder be nominated as the cooled-wet electrode.

2. Description of the Prior Art

Although surgical resection is still considered as a primary option for the treatment of malignant tumors, minimally invasive alternatives including intraoperative cryosurgery, local injection of ethanol, microwaves, interstitial laser therapy focused ultrasound and radio frequency (RF) tissue ablation have been developed in order to ablate the tumor less invasively for the safety of the patient and reduction of the costs and/or to broaden our capability in treatment of the patient.

Among these approaches, RF ablation has shown the greatest impact on recent experimental and clinical research because of its low invasiveness, simplicity and favorable cost-effectiveness.

In RF ablation the radio-frequency waves are emitted from a generator through an uninsulated part of the electrode which is inserted into a target tissue. The tissue destruction in a form of coagulation necrosis is caused primarily by resistive heating in the surrounding tissue and secondarily by the peripheral passive heat conduction.

Resistive heating is proportional to the square of the distance between the central electrode and adjacent tissue. Therefore, significant resistive heating only occurs within a rim of tissue in direct contact with the electrode. Beyond this rim, the tissue is further heated as a result of passive conduction of increased temperature. However, the RF emission is readily terminated as a result of impedance rise at the electrode-tissue interface, which is secondary to tissue desiccation and carbonization. Due to such non-optimal RF energy delivery and dissipation, the lesion size induced by known prototypes electrodes is smaller than 2 cm, which is obviously insufficient for tumor ablation. Similar to the principle in surgical resection, the ideal range of RF tissue destruction should involve the entire tumor and a layer of adjacent normal tissue as a safety margin to avoid incomplete ablation.

Many known technical innovations have been made to increase the lesion size in RF ablation. These include the introductions of:

1) bipolar electrodes;
2) a cooled electrode and cooled-clustered electrodes;
3) a "wet" electrode with hypertonic saline infusion; and
4) an expandable electrode.

According to the principle of minimal invasiveness, a monopolar is preferred to multipolar electrode.

As shown in table 1, although markedly increased, the lesion sizes induced by these modified devices are still limited, normally less than 4 cm in diameter. If a tumor larger than 2 cm, there is little chance to achieve complete ablation by a single session. Therefore there is still a demand to further optimize these devices and techniques.

Table 1 shows the lesion sizes induced by different known designs of electrode in RF Ablation.

TABLE 1

| Electrode Type | Lesion size (cm) | No. Reference |
| --- | --- | --- |
| Prototype Electrode | 0.8–1.5 | 1 |
| Bipolar Electrode | 5 (the width between poles) | 2 |
| Cooled Electrode | 1.4–3.6 | 3 |
| Wet Electrode | 4.5 ± 0.75 | 4 |
| Expandable electrode | 4.5 | 5,6 |
| Cooled-clustered | 4.7 ± 0.1 | 7 |

References cited are:
1 Goldberg, S. N. et al. (Academic Radiology 1995;2:399–404)
2 Goldberg, S. N. et al. (Acad. Radiol. 3/929, 1996)
3 Lorentzen, T. A. (Acad. Radiol. 3:556, 1996)
4 Miao, Y. et al. (J. Surg. Res. 71:19, 1997)
5 Rossi, S. et al. (AJR. Am. J. Roentgenol., 170:1015–1022, 1998)
6 Patterson E J, et al. (Ann Surg, 227:559–565, 1998)
7 Goldberg S. N. et al. (Radiology 209:371–379; 1998)

SUMMARY OF THE INVENTION

The main object of the invention is to provide new device and methods yielding good RF ablation results and providing larger lesion size. In particular whereby the lesion size is larger than 5 and preferably more than 6 cm.

According to the invention this is realized by a combination of separately known features, which in combination surprisingly results in a more effective RF ablation. This is realized by an increased conductivity of the target tissue as well as at the electrode tissue interface in relation to a decreased tip temperature.

The invention therefore provides a device for delivering radio-frequency energy combining the characteristics of a "wet" electrode and of a cooled electrode.

A main object is a minimal invasiveness of the radio-frequency ablation technique. A minimal invasiveness is obtained by a precise puncturing and guidance towards the tissue to be treated. It is therefore a further object of the invention to improve the efficiency of the puncturing and guidance of the radio-frequency electrode and more broadly of all instruments used in RF ablation. The puncturing is presently performed by the sharpened distal end of the electrode. As this distal end is often open introduction sometimes causes obstruction and once introduced blocks off these openings at the distal tip. It will be understood that the use of guidance means is not necessary for the use of the cooled wet electrode. The puncturing can be performed by the sharpened distal end of the cooled wet electrode as sole puncturing mean.

As a solution to this disadvantage the invention provides further a separate guidance element for the guidance of an instrument, in particular a radio-frequency electrode. The guidance element according to the invention is substantially formed by a open hollow shaft having a cylindrical central bore which is adapted in dimensions for the temporarily housing and axial displacement of an instrument during radio-frequency ablation procedures. Said instrument-can be for example a puncturing needle for a smooth introduction towards the tissue to be treated, a radio-frequency electrode for the radio-frequency ablation step and further a biopsy needle or biopsy clamp for providing proof of the efficiency of the radio-frequency ablation procedure by the collection of a tissue sample.

It will be understood that several cooled wet electrodes, for example two, three, four or more can be used as a clustered cooled wet electrode device when the tumor to be treated is of an excessive dimension.

BRIEF DESCRIPTION OF THE DRAWINGS

The invention shall be elucidated hereunder with reference to the drawing wherein schematically is shown in.

DETAILED DESCRIPTION OF THE PREFERRED EMBODIMENTS

Figure 2:
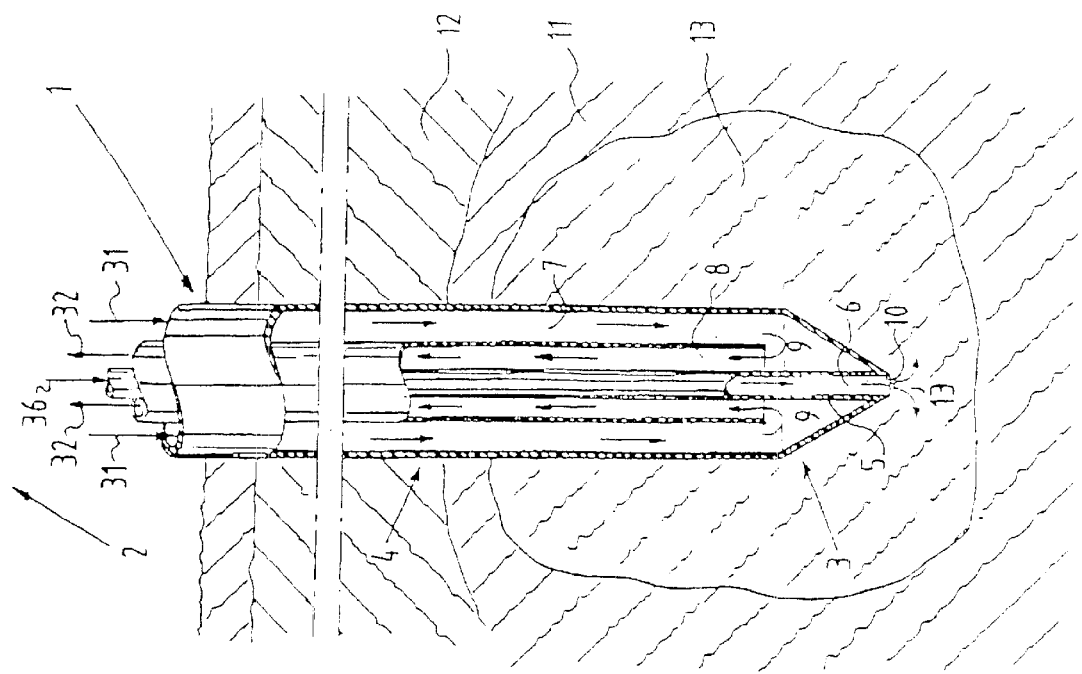
FIGS. 1 to 7 partially broken away cross-sectional and perspective views of five preferred embodiments of the cooled-wet electrode according to the invention.
Figure 1:
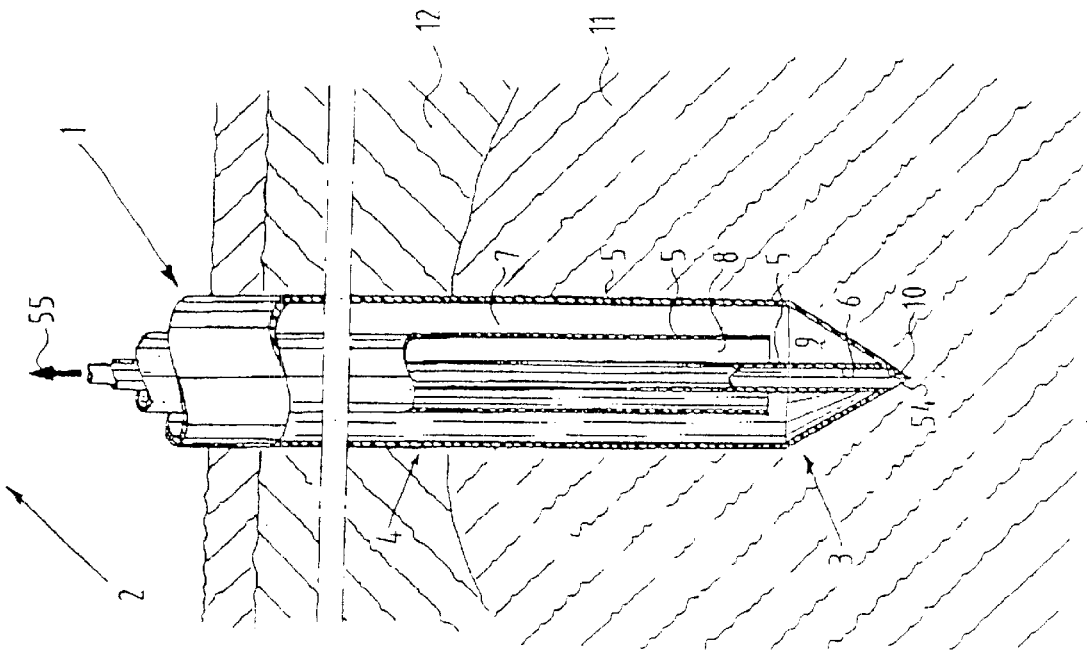

In the Figures the thin printed arrows define the flow pattern of a cooling medium and a wetting medium and the bold printed arrows the direction of the movement of parts of the electrode. The cooling and wetting medium are preferable solutions and in a preferred embodiment the wetting solution is a saline solution and more preferably a hypertonic (for example 0.9% saturated) saline solution. The cooling solution is preferably water or cooled media such as 0° C. saline.

A rigid hollow needle electrode 1 comprises a proximal end 2, a distal end 3 and there between a longitudinal part 4. The electrode 1 comprises a number of cylindrical wall elements 5 forming three concentric channels, i.e. an inner concentric channel 6 and two outer concentric channels 7, 8, which outer concentric channels 7, 8 are connected at the distal end 3 of the electrode 1 forming a closed loop 9. The outer concentric channels 7, 8 define a flow path for a cooling solution such that at least the distal end 3 of the electrode 1 can be sufficiently cooled.

The inner concentric channel 6 is open 10 at the distal end 3. The inner concentric channel 6 defines the flow path for the wetting solution and a housing for puncturing means which is formed by an axial (arrow 55) retractable and protruding pith organ 54. The pith organ 54 closes the open end 10 when being inserted into the target tumor 11 in order to avoid obstruction in the channel 10. An accesory biopsy needle of the same size can be replaced before ablation for sampling tumor tissue for histopathologic examination. After insertion of the electrode 1 the pith organ 54 is retracted upwards making free the flowing path of the wetting solution in the channel 6 (FIG. 2). When the electrode 1 is introduced towards a tumor 11 on a target organ 12 radio-frequency energy will be delivered via a non-insulated part of the electrode 1, being at least the distal end 3 of the electrode 1 while simultaneously the distal end 3 is cooled by a cooling solution and the proximity of the distal end 3 is being wetted 13 by a wetting solution. The distal end 3 of the electrode 1 is preferably sharpened such that is has a further puncturing function. The separate flow control of the cooling and wetting for example in concentration, temperature, etc. results in a superior lesion size.

The electrode 1 has in general a substantially rigid structure in order to be able to be aimed precisely in the tumor.

The axial slidable pith organ 54 is used in order not to obstruct the channel for the wetting solution 6. Once the electrode 1 is positioned in the centre of the tumor 11 the pith organ 54 is upwardly retracted and removed. A RF-energy delivery can start when the pith 54 is retracted and the wetting solution 13 is delivered simultaneously with the RF-energy.

Figure 3:
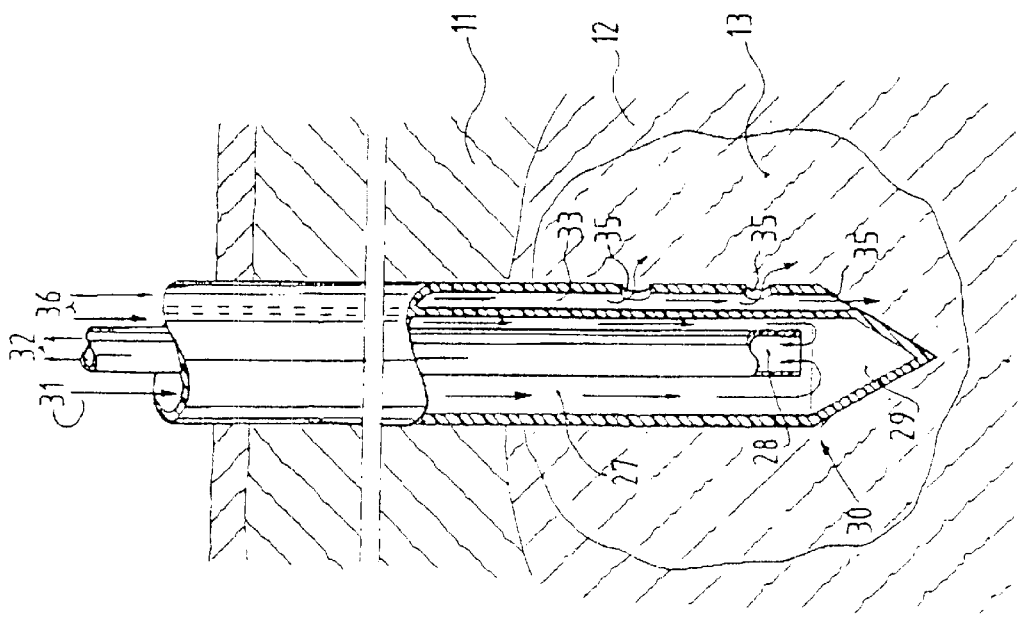

The embodiment disclosed in FIG. 3 comprises two concentric channels 27 and 28 forming a closed loop at the closed end 29 of the distal end 30. This closed loop channel (27,28) defines the flow channel for the cooling solution as arrows 31 (down) and 32 (up) indicate (comparable to FIG. 2). At the distal end 30 an open lateral channel 33 is provided as flow path for the wetting solution, which is preferably a hypertonic saline solution. At the distal end 30 the channel 33 is provided with multiple openings 35 for the outflow of the wetting solution 13 in order to create sufficient spreading of the wetting solution 13 at the proximity of the distal end 30. Arrows 36 (down) and 35 (out) define the flow path for the wetting solution.

The diameter of these needle electrodes should preferably be as small as possible and is preferably smaller than 3 mm.

Figure 4:
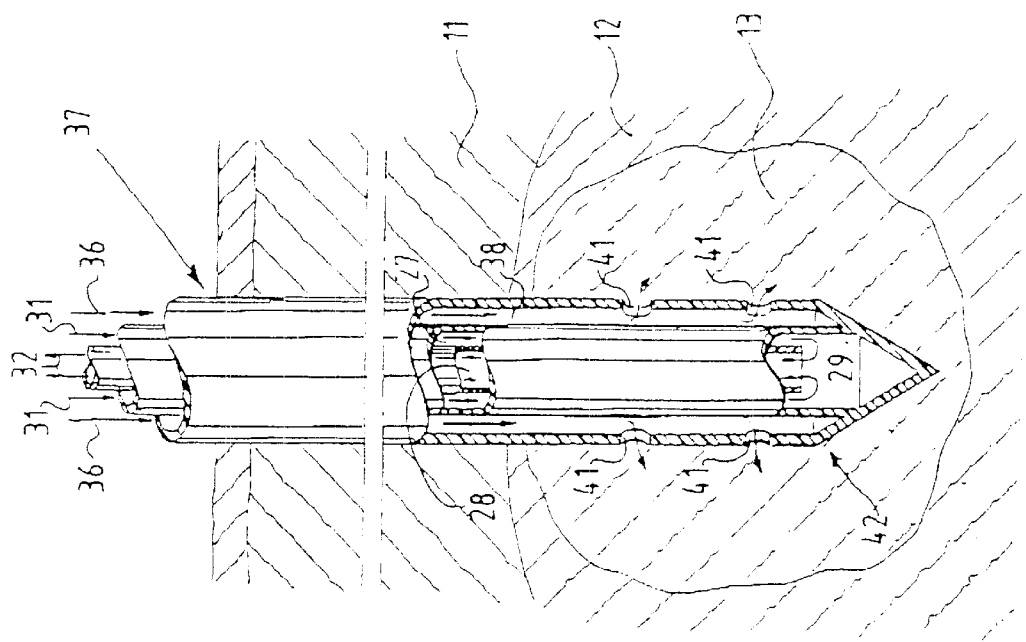

The embodiment of the electrode 37 depicted in FIG. 4 comprises three concentric channels: an outer channel 38 provided with multiple holes 41 at the distal end 42 of the electrode 37 and two concentric channels 27 and 28 forming a closed loop 29 at the distal end 42 of the electrode 37 and defines the flow path for the cooling solution.

Figure 5:
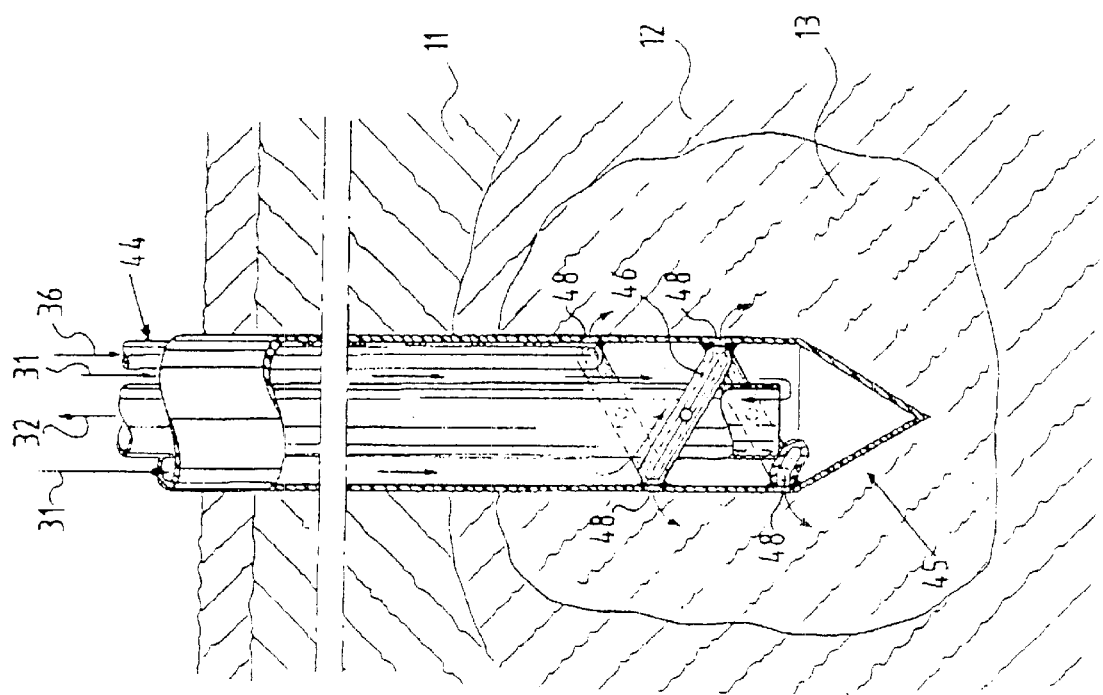
Figure 9C:
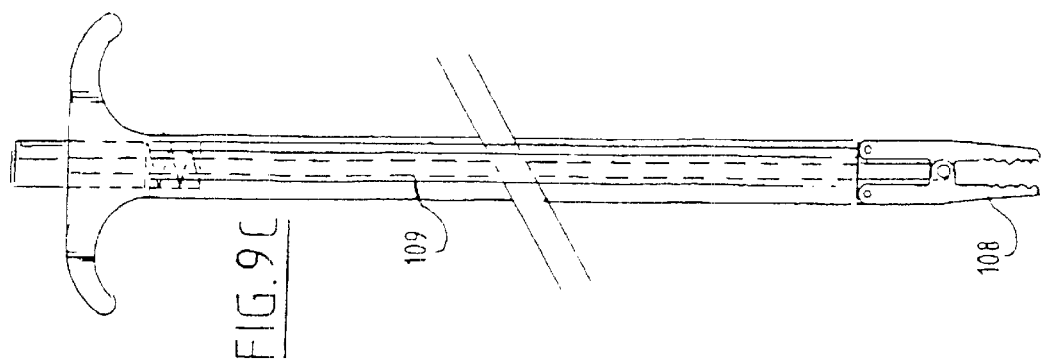
FIG. 9 a partial broken away perspective view of a guidance element (FIG. a), a puncturing needle (FIG. b) and a biopsy needle (FIG. c).
Figure 9B:
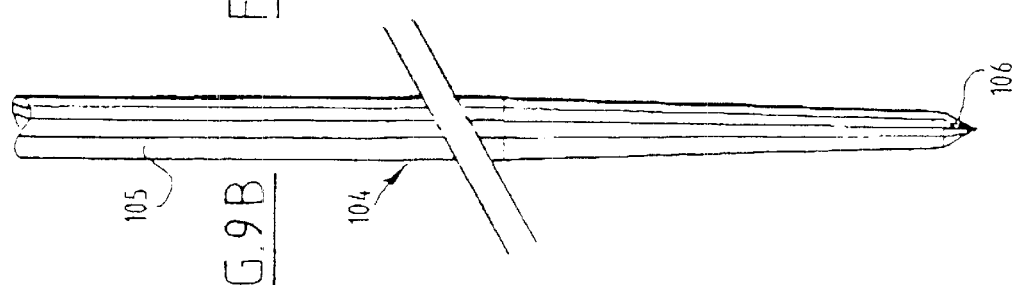
Figure 9A:
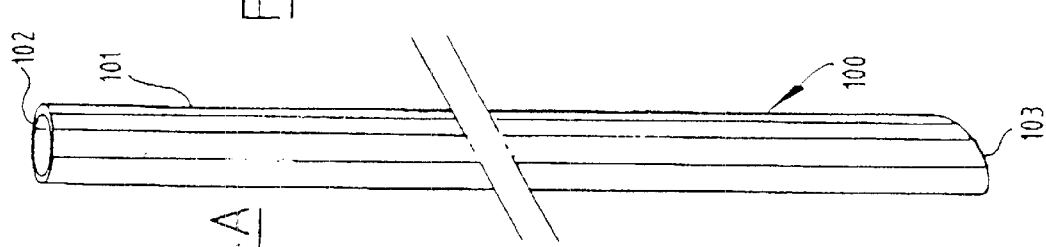

The electrode of FIG. 5 discloses another preferred embodiment wherein a separate lateral channel 44 for the wetting solution 13 is provided having at the distal end 45 of the electrode a helical formed part 46 around the distal end 45 of the electrode and is provided with multiple openings 48 in order to create a flow path for the wetting solution through and out the electrode.

Figure 6:
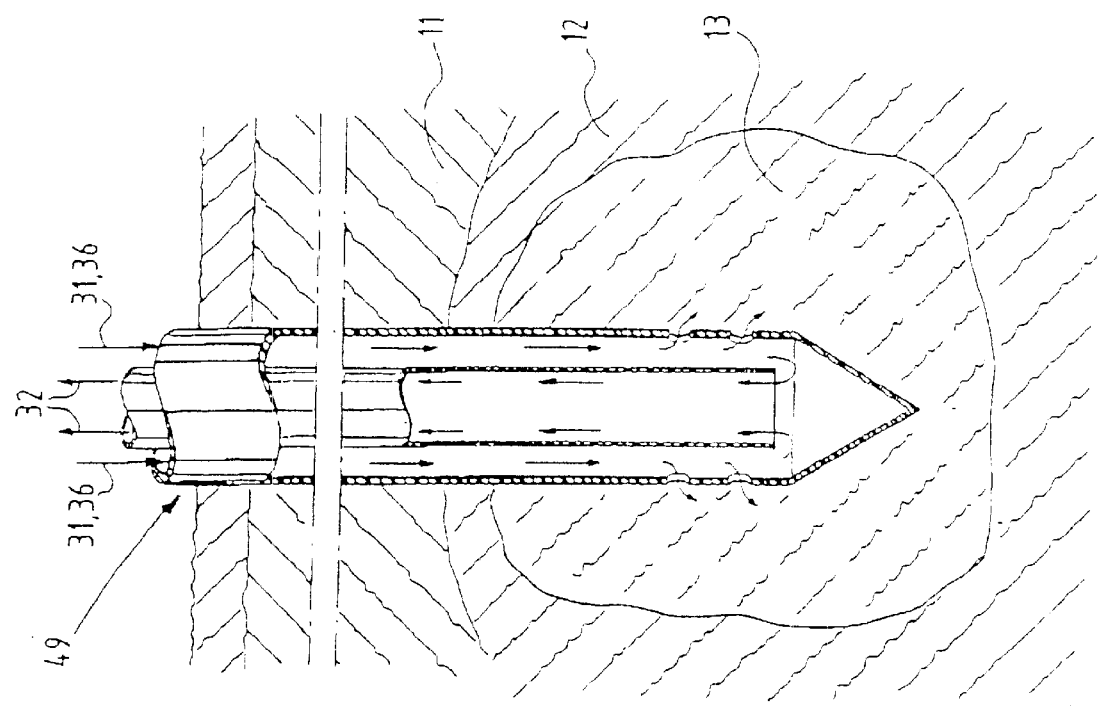

In the embodiment of FIG. 6 the cooling and wetting solution is one and the same thus. This has the advantages of a more compact and simpler structure of the electrode 49. However, in the other embodiments the separate flow rate can be adjusted for their purposes i.e. the cooling solution normally has a higher flow rate than the wetting solution.

Figure 7:
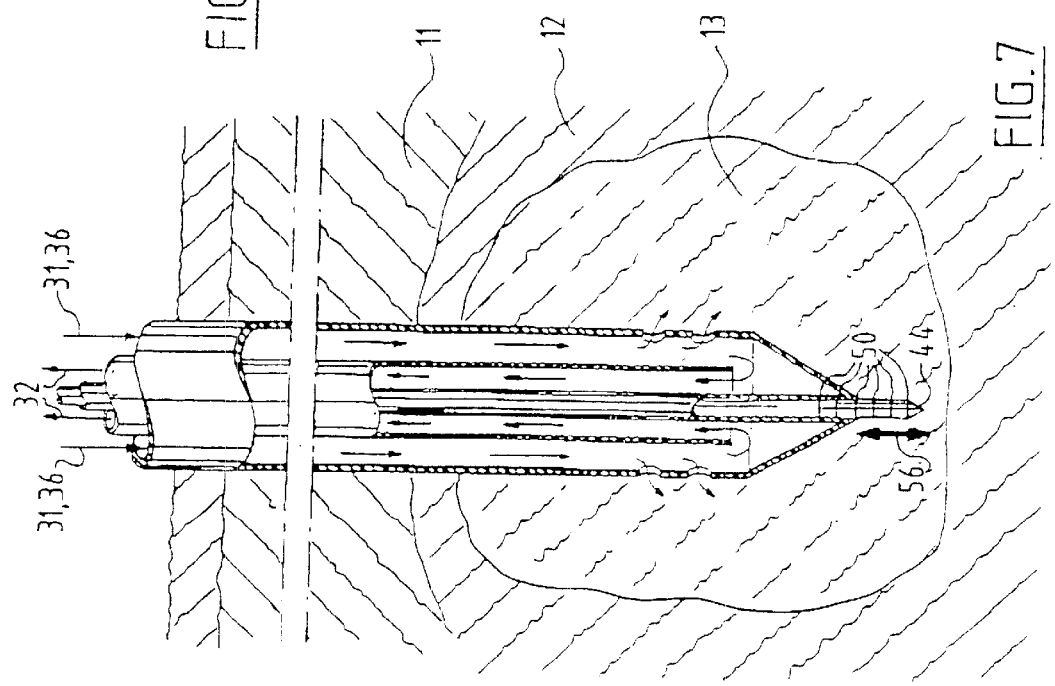

The embodiment of FIG. 7 discloses a further preferred embodiment comprising an axial (arrow 56) slidable temperature measurement organ 44 comprising multiple thermosensors 50 on a determined distance of each other. Normally radiofrequency radiation and energy will spread radially in relation with the distal end of the electrode. The retractable thermosensor will provide in an objective manner a measurement of the efficiency of the radiofrequency ablation method.

The use of these concentric channels does not only provide the advantage of a sufficient and controlled flow rate but also the synergetic effect that the wetting solution is simultaneously cooled off.

It is obvious for a skilled man that any combination of the form or the position of the channels, the described central pith and the retractable thermosensor can be varied, for example the central thermosensor can be positioned laterally, also the pith can be positioned in a different manner without departing from the scope of the invention.

Figure 8:
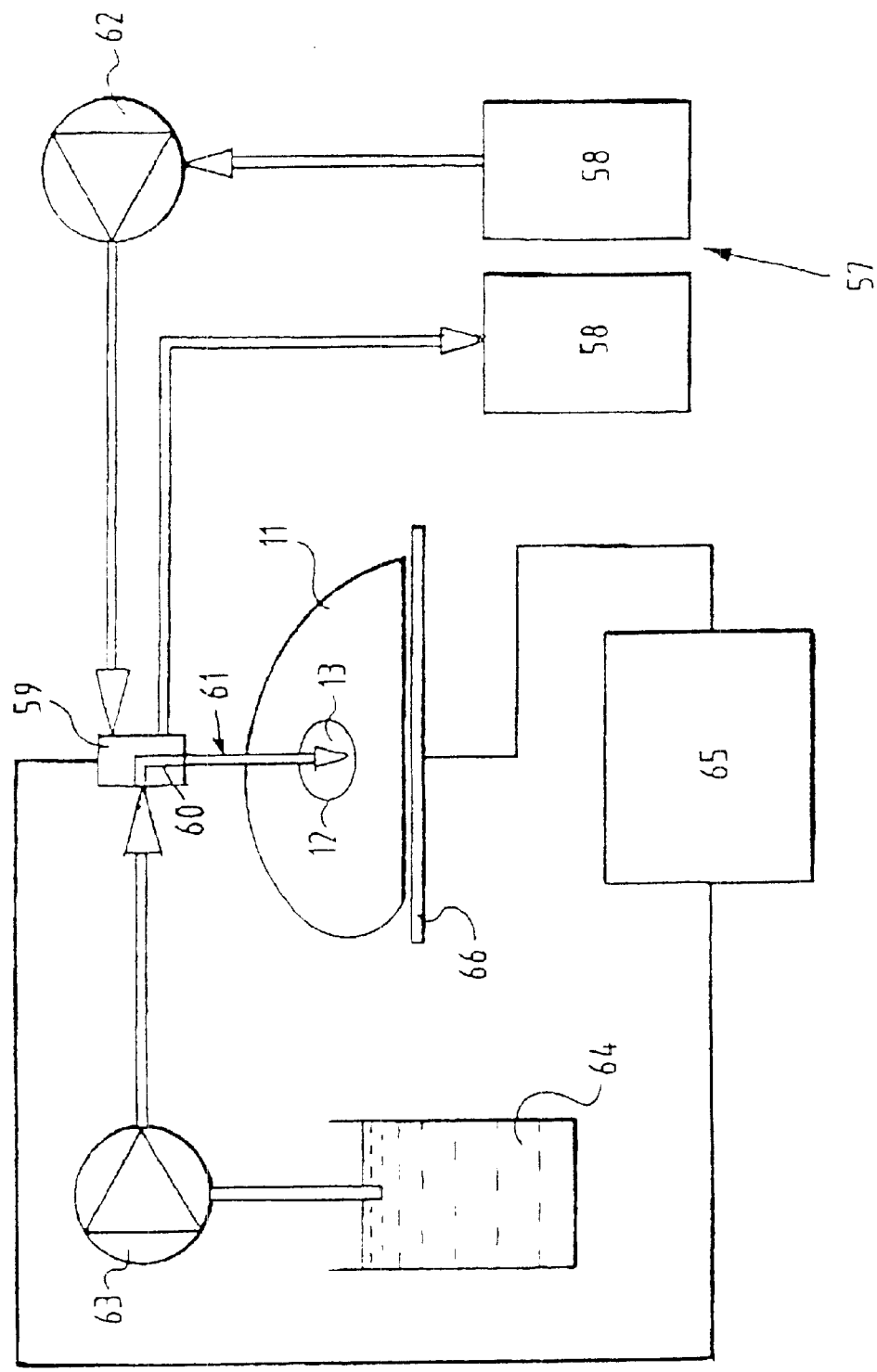
FIG. 8 a schematic illustration of radio-frequency ablation system using a cooled-wet electrode according to the invention.

FIG. 8 depicts a schematic illustration of the radio-frequency ablation of a target tissue 11, for example the liver with a cooled-wet electrode of the invention. The cooling means 57 comprise in general a reservoir 58 for a cooling solution connected to an opening 59 at the proximal end 60 of an electrode 61 and further comprising circulation means 62 in order to circulate the cooling solution.

The wetting means generally contain an infusion pump 63 connected to a hypertonic solution 64 and connected to the opening 59 at the proximal end 60 of the electrode 61. The proximal end 60 of the electrode 61 is connected to a radio-frequency energy source 65 and in order to close the electric circuit a ground path 66 is provided under the organ 11. The lesion size is substantially enlarged by using a cooled/wet electrode of the invention up to 6–10 cm.

If appropiate temperature control means are further provided at the distal end of the electrode to monitor and to control the temperature. All the depicted configurations of channels and elements in or on the electrode are, as is obvious adjustable and combinable or interchangable.

Guidance element 100 is substantially formed by an open elongated shaft 101 provided with a central cylindrical bore 102 and a open blunt distal end 103. The diameter of the cylindrical bore 102 is thus adjusted that instruments to be guided by the guidance element 100 can be introduced and be displaced in the axial direction of the bore with a minimal radial tolerance but still providing smooth axial guidance. The puncturing can preferably be performed by a puncturing needle 104 which is introduced in the guidance element 100 and provided with a sharpened distal end 106 being used as a puncturing mean for introducing of the combination guidance element 100 and needle 104 towards to the tissue to be treated. A smooth introduction can be obtained due to the sharpness and to the form and dimensions of the needle 104. Once introduced the needle 104 is retracted out of the cylindrical bore 102 of the guidance element 100 while maintaining the introduced position of the guidance element 100. A radio-frequency electrode can then be entered through the cylindrical bore 102 of the guidance element 100 until protruding at the distal end of the guidance element 100. When the radio-frequency ablation procedure is terminated, the electrode is retracted out of the guidance element 100, while this element is maintained in the previous obtained position.

For providing proof of the efficiency of the radio-frequency ablation a biopsy needle 109 can be introduced through the same cylindrical bore of the guidance element 100 towards the treated tissue. The distal end of the biopsy needle 109 is provided with a clamp 108 for collecting treated tissue samples for further investigation.

The advantages and the specific characteristics of the cooled-wet electrode are founded on the following experiments.

Materials and Methods of the Experiments
The subjects of RF ablation are:

1. Commercial beef liver: 4 pieces of beef livers of about 10 kilograms each were purchased from a local butcher. The temperature of the liver was warmed up from 4° C. to room temperature before RF ablation.
2. Swine liver: fifteen livers were excised from the pigs and immediately brought to the site of RF ablation.
3. Twelve domestic pigs of 40–60 kg body weight.

The used equipment comprised a demo RF generator (RFG-3E, Radionics, USA); a cooling pump: Watson-Marlow 31.3 (Watson-Marlow Limt. England); a wetting saline infusion pump (Ismatic, Switzerland); cool-wet electrodes according to the invention and a MRI scanner: 1,5 Tesla Mangetom Vision (Siemens, Erlangen, Germany).

Experimental Groups ex vivo Tests
1. Group A: Conventional RF mode, 22 sites of ablation (without cooling perfusion and saline infusion)
2. Group B: Cooled only mode: 27 sites of ablation (RF at 50 W for 10 min with cooling perfusion at 40 ml/min)
3. Group C: Wet only mode: 20 sites of ablation (RF at 50 W for 10 min with 5% saline infusion at 1 ml/min)
4. Group D: Continuing cooled-wet mode, 20 sites of ablation (RF at 50 W for 10 min with 5% saline infusion at 1 ml/min and cooling perfusion at 40 ml/min)
5. Group E: Cooled-wet mode with disconintuing saline infusion, 20 sites of ablation (RF at 50 W for 10 min with cooling perfusion at 40 ml/min and 5% saline infusion at 1 ml/min for only first 5 min)
6. Group F: Cooled-wet mode with discontinuing cooling perfusion, 13 sites of ablation (RF at 50 W for 10 min with 5% saline infusion at 1 ml/min and cooling perfusion at 40 ml/min and for only first 5 min)
7. Group G: RF of cooled-wet mode by manual control at 70–90 W during 10–30 min:10 sites.

In vivo Liver Ablation in the Swine
Under general anesthesia and intubated ventilation, 12 swines were laparotamized with left and right liver lobes exposed for RF ablation. Under laparotomy, 72 RFA lesions were created in 12 pigs using a novel "cooled-wet" elecrode that combines internal cooling perfusion and hypertonic saline interstitial infusion. Both power control mode (Group A. cooled only, B. wet-only and C. cooled-wet) at 90 W and manual control mode (Group D. cooled-only, E. wet-only and F. cooled-wet) were compared for impedance, current and lesion size. MRI was performed for measurement of lesion size. T1 and T2 weighted MR1 were performed immediately after RF ablation.

The results in ex vivo tests with excised pork and beef livers are summarized in table 2. RF ablation at 50 W for 10 min created the largest lesion size with cooled-wet mode (group D) right than with any other modes left. Continuity of RF energy delivery was ensured only in group D, so that the lesion size reached close to 10 cm if ablation duration was prolonged to 30 min and the power was set to 70–90 W. Due to a sudden increase of impedance in other groups sooner or later after ablation started, the delivery of RF energy almost ceased and the lesion size did not further increase.

TABLE 2

| Group | No. Sites | Saline Infusion (ml/min) | Tip Cooling Perfusion (ml/min) | Tip Temp. (° C.) | Power Output (W) | Impedance (Ō) | Current (A) | Lesion Size (cm) |
|---|---|---|---|---|---|---|---|---|
| A | 22 | 0 | 0 | 93.6 ± 3.9 | 13.7 ± 1.5 | >900 | 0.13 ± 0.1 | 0.86 ± 0.3 |
| B | 24 | 0 | 40 | 31.5 ± 4.8 | 16.1 ± 3.3 | 81.2 ± 16.5 | 0.85 ± 0.1 | 2.43 ± 0.5 |
| C | 18 | 1 | 0 | 99.6 ± 0.9 | 45.2 ± 10.8 | 99.8 ± 113.4 | 0.94 ± 0.4 | 3.80 ± 0.5 |
| D | 20 | 1 | 40 | 35.9 ± 6.8 | 49.5 ± 2.4 | 55.8 ± 50.7 | 1.14 ± 0.2 | 4.90 ± 0.6 |
| E | 20 | 1 × 5 min | 40 | 42.9 ± 4.4 | 17.8 ± 2.7 | 725.6 ± 229.3 | 0.15 ± 0.0 | 3.89 ± 0.6 |
| F | 13 | 1 | 40 × 5 min | 99.5 ± 0.9 | 38 ± 12.2 | 412.5 ± 138.3 | 0.46 ± 0.4 | 4.27 ± 0.5 |

Notes:
1. Group A: Conventional RF mode, (without cooling perfusion and saline infusion)
2. Group B: Cooled only mode (RF at 50 W for 10 min with cooling perfusion at 40 ml/min)
3. Group C: Wet only mode (RF at 50 W for 10 min with 5% saline infusion at 1 ml/min)
4. Group D: Continuing cooled-wet mode according to the invention (RF at 50 W for 10 min with 5% saline infusion at 1 ml/min and cooling perfusion at 40 ml/min)
5. Group E: Cooled-wet mode according to the invention with discontinuing saline infusion (RF at 50 W for 10 min with cooling perfusion at 40 ml/min and 5% saline infusion at 1 ml/min for only first 5 min)
6. Group F: Cooled-wet mode according to the invention with discontinuing cooling perfusion at 40 ml/min for only first 5 min).

The swine tolerated in the in vivo tests the RF ablation well and life signs were kept normal during and after ablation. The lesion size appeared smaller than that in ex vivo tests probably due to the cooling effect from hepatic inflow. In vivo results: together with lower impedance and higher power output, the lesion sizes in group C (4.8±0.6 cm) and F (6.5±0.8 cm) were significantly larger (P<0.01) than that in group A (2.4±0.5 cm), B (3.1±1.0 cm), D (3.3±0.6 cm) and E (3.5±0.9 cm).

In RF ablation with a cooled electrode, the inner cavity channel of the electrode is preferably irrigated with cold or tap water. By the cooling effect, the distal end tip of the electrode is maintained at low temperature and free of charring thereby facilitating the conductivity of electrode-tissue interface and preventing an impedance rise. However, to a certain extent, the lesion size can no longer be further increased, because 1) the dimension of the electrode and hence the adjacent areas ablated with resistive and conductive heating are limited;
2) the conductivity of the tissue itself is relatively low if no external conductive agent is added;
3) steaming and tissue desiccation always occur next to the electrode-tissue interface which causes a rise of impedance.

The technique of a wet electrode and of a cooled electrode were separately known and eventuate in several drawbacks.

In RF ablation with a wet electrode, a hyper-conductive saline as an example of a wetting solution is prior and continuously infused via a the electrode into the target tissue while RF energy is delivered. The conductivity of 0,9% normal saline is 3–5 times higher than that of the blood and 12–15 times higher than that of tissues. With more than 5 times of increased concentration, further improvement of conductivity is expected. Infused saline functions as a "liquid electrode" within the tissue to be ablated and spreads applied RF energy away from the metal electrode to the surrounding tissue. Therefore, both the central resistive heating rim and peripheral passive heating area are increased, hence a larger lesion can be obtained. When saline is infused, some convective cooling also occurs at the tip. Besides, steaming is retarded by the increased boiling temperature of tissue fluid in which hypertonic saline is added. The effect of RF ablation with saline infusion appears already superior to that with cooling perfusion. However, this was still not optimal. The tip temperature still frequently raises above the boiling temperature at the electrode-tissue interface. Furthermore, infusion of a large amount of saline into the tumor may increase the static interstitial pressure which in turn may force individual tumor cells to migrate into adjacent or remote areas.

As demonstrated in our experiments, the current invention of cooled-wet electrode combines the advantages and meanwhile overcomes the disadvantages of each separate technique, yielding an optimal result of RF ablation with lesion sizes larger than 6 cm. This is realized by an increased conductivity of the target tissue as well as at electrode-tissue interface and a decreased tip temperature. The amount of infused saline can be reduced in comparison to that in "wet" alone mode. Unlike other more invasive approaches such as RF with bipolar, clustered and expanded electrodes and multiple applications of a single electrode, the present cooled-wet embodiment only use a single needle, through a single puncture but cause a large lesion ideal for tumor ablation or eradication. The proposed cooled-wet electrode and the described procedure allows to obtain by a single needle and in one session, a lesion of sufficient size. This is in contrast with the currently existing devices which necessitate either multiple deliveries of expanded electrodes or multiple applications of a single electrode to obtain similar results. Obviously, the application of a single electrode in one session is easier to perform and to control.

What is claimed is:

1. A device for delivering radio frequency (RF) energy, for example during tissue ablation procedures, comprising:

an electrode having an uninsulated distal end and a proximal end connectable to a radio frequency energy source, and wetting means for wetting the distal end of the electrode and the proximity thereof with a non-toxic (RF) conductive solution wherein the wetting means comprise a first channel which defines a flow path for the wetting solution, wherein tissue puncturing means are associated either with the distal end of the electrode or with an inner axial slidable pith organ and wherein the device further comprises cooling means for cooling at least the distal end of the electrode, which cooling means comprise a second channel which defines a flow path for the cooling solution, wherein the wetting channel is open at the distal end of the electrode and wherein the cooling channel is closed at the distal end of the electrode, with the cooling channel and the wetting channel being mutually isolated.

2. The device according to claim 1, wherein the first and second channels are concentric.

3. The device according to claim 1, wherein the channel defining the flow path for the wetting solution is helical and is formed at the distal end of the electrode around an inner channel for the cooling solution and said helical wetting channel comprises several openings at the distal end.

4. The device according to claim 1, wherein the tissue puncturing means are formed by an inner axial slidable pith organ.

5. The device according to claim 1, wherein the distal end of the electrode is provided with retractable temperature control means preferably comprising at least two temperature sensors.

6. The device according to claim 1, wherein the electrode is formed by a cluster of several separate electrodes in a parallel alignment.

7. The device according to claim 1 further including a guidance element for the guidance of the displacement of an instrument in radio-frequency ablation procedures which guidance element is substantially formed by an open hollow shaft having a central cylindrical bore.

8. The guidance element according to claim 7, wherein said instrument is chosen from a puncturing needle, a radio-frequency ablation electrode or a biopsy needle.

9. A process for cooling and wetting a radio frequency energy delivering device as defined in claim 1, comprising the steps of providing a wetting solution to the proximity at a distal open end of the frequency energy delivering device and providing a cooling of the distal end of said device by transport of a cooling solution in the inner body of said device.

10. The process according to claim 9, wherein the temperature at the proximity of the distal end is monitored by providing multiple temperature measurement means at different distances from the distal end of the electrode.

* * * * *